United States Patent [19]

Schwartz, Jr.

[11] Patent Number: 5,395,858
[45] Date of Patent: Mar. 7, 1995

[54] PROCESS FOR RECYCLING POLYESTER

[75] Inventor: John A. Schwartz, Jr., Spartanburg, S.C.

[73] Assignee: Partek, Inc., S.C.

[21] Appl. No.: 234,237

[22] Filed: Apr. 28, 1994

[51] Int. Cl.$^6$ ............................................. C08J 11/04
[52] U.S. Cl. ........................................ 521/48; 521/45;
75/413; 75/417; 75/422; 528/481; 528/489;
528/499
[58] Field of Search ...................... 521/45, 48; 75/417,
75/422, 713; 528/481, 489, 499

[56] References Cited

U.S. PATENT DOCUMENTS

| | | |
|---|---|---|
| 3,047,435 | 7/1962 | Wemple . |
| 3,120,561 | 2/1964 | Chambret . |
| 3,257,335 | 6/1966 | Whitfield et al. . |
| 3,503,904 | 3/1970 | Dietz et al. . |
| 3,544,622 | 12/1970 | England . |
| 3,594,414 | 7/1971 | Katzschmann . |
| 3,647,422 | 3/1972 | Wainer . |
| 3,652,466 | 3/1972 | Hittel et al. . |
| 3,873,314 | 3/1975 | Woo et al. . |
| 3,884,850 | 5/1975 | Ostrowski . |
| 3,928,253 | 12/1975 | Thornton et al. . |
| 3,953,502 | 4/1976 | Fassell et al. . |
| 3,956,088 | 5/1976 | Fassell et al. . |
| 4,078,143 | 3/1978 | Malik et al. . |
| 4,163,860 | 7/1979 | Delattre et al. . |
| 4,324,705 | 4/1982 | Sero et al. . |
| 4,355,175 | 10/1982 | Pusztaszeri . |
| 4,392,889 | 7/1983 | Grout . |
| 4,578,502 | 3/1986 | Cudmore . |
| 4,578,510 | 3/1986 | Doerr . |
| 4,602,046 | 7/1986 | Buser et al. . |
| 4,605,762 | 8/1986 | Mandoki . |
| 4,612,057 | 9/1986 | Buser et al. . |
| 4,620,032 | 10/1986 | Doerr . |
| 4,626,598 | 12/1986 | Packer et al. . |
| 5,064,466 | 11/1991 | Hilton . |
| 5,095,145 | 3/1992 | Rosen . |
| 5,120,768 | 6/1992 | Sisson . |

FOREIGN PATENT DOCUMENTS 0497662A  1/1992  European Pat. Off. .

OTHER PUBLICATIONS

Research Disclosure Jan. 1981, p. 28, #20130, Silver Recovery and Polyester Recycling from Photographic Film Scrap; Clelland, et al.

Research Disclosure Dec. 1981, pp. 449–450, #21231, Separation of Polyvinylidene Chloride Copolymer Coatings from Oriented Polyester Substrates.

*Primary Examiner*—Samuel A. Acquah
*Attorney, Agent, or Firm*—Dority & Manning

[57] ABSTRACT

A process for recycling polyester contained in waste materials is provided. The polyester is converted into ethylene glycol and terephthalic acid. The process steps generally include first combining materials containing polyester with an alkaline solution to form a slurry. The slurry is heated, causing ethylene glycol to evaporate which can then be collected. The remaining product stream is then mixed with water and filtered to remove any undissolved impurities. The aqueous filtrate can be acidified causing terephthalic acid to precipitate. Further, if silver is contained within the materials fed to the process, the silver can also be isolated and recovered.

27 Claims, 1 Drawing Sheet

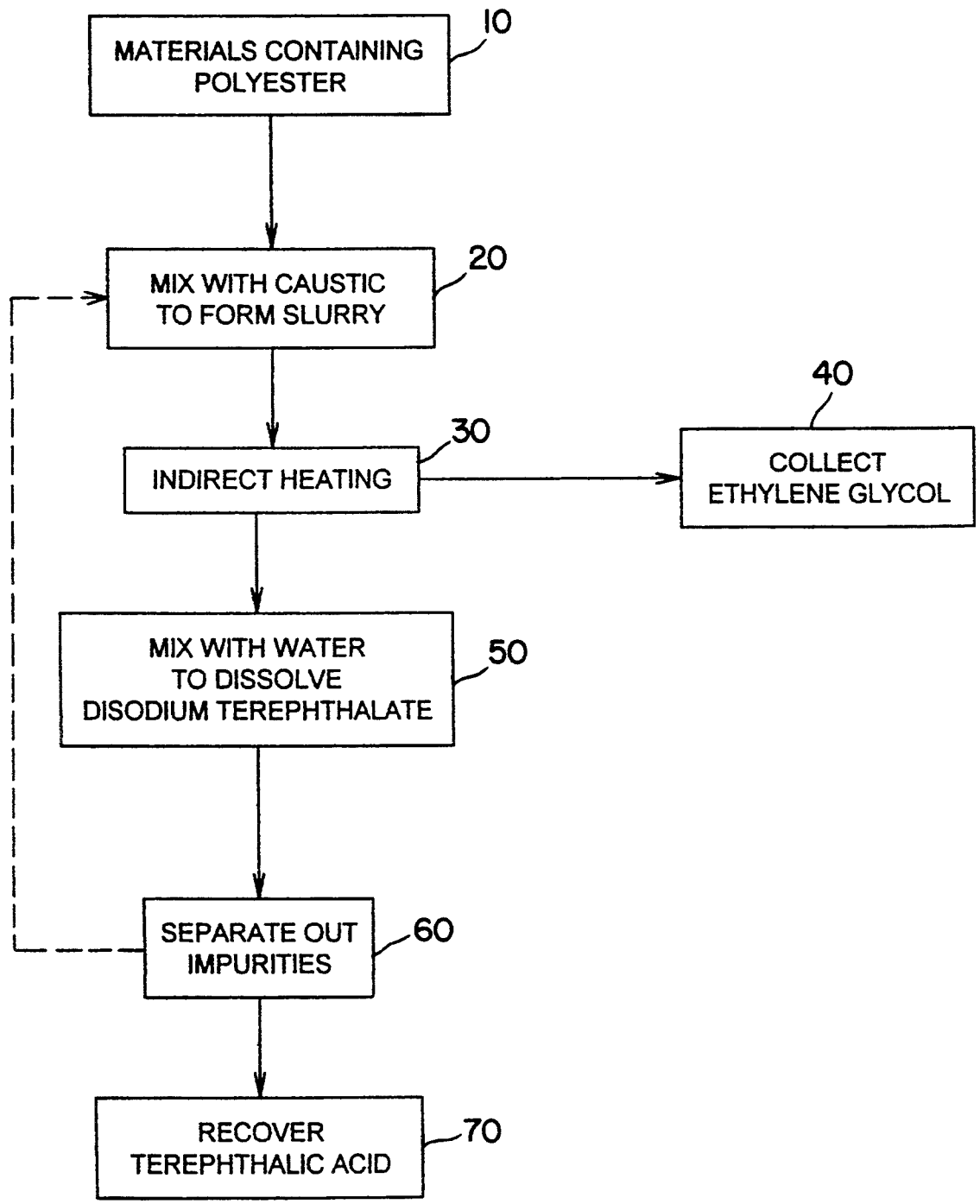

PROCESS FOR RECYCLING POLYESTER

BACKGROUND OF THE INVENTION

The present invention generally relates to a process for recycling polymeric materials and more particularly to a process for converting polyester into its original chemical components: ethylene glycol and terephthalic acid.

Polyester is a polymeric material made from the esterification of polybasic organic acids with polyhydric acids. Specifically, polyester is commonly manufactured by reacting terephthalic acid with ethylene glycol resulting in a compound known chemically as polyethylene terephthalate and commonly as PET. Widely known polyesters include Dacron and Mylar.

PET is currently being used as a polymeric base material in a wide variety of applications. For example, polyester is commonly used to make photographic films, X-ray films, bases for magnetic coating such as in recording tapes, beverage containers, surgical aids such as synthetic arteries, and as a fabric for making garments and other similar items. However, although polyester is very useful, waste materials containing polyester are beginning to create a waste management and disposal problem.

Currently, those skilled in the art are seeking different methods of recovering and reusing polyester contained in waste plastic products. However, recovery of polyester from waste products has been found difficult. In particular, many prior art processes are not capable of efficiently or economically recovering polyester when a significant amount of impurities and contaminants are present. Such impurities include cellulosic materials, polymeric materials and metals. As such, most attempts have been limited to mechanical recovery processes directed to specific polyester-containing materials. In these systems, the waste materials are merely washed in order to recover polyester films.

For example, U.S. Pat. No. 4,602,046 to Buser et al., discloses a method for the recovery of polyester from scrap material such as photographic film having a polyester base and at least one layer of macromolecular organic polymer. Specifically, scrap material is cut or chopped into small individual pieces or flakes and treated in a caustic alkaline solution at a solids level of at least 25% by volume and under conditions of high shear. The organic polymer coating material is removed from the polyester flakes. The polyester flakes are then separated from the polymer coating material by filtration or centrifugation, rinsed in water, and dried. The recovered polyester flakes can be used as a feed stock for making films, bottles or other polyester articles.

A method and apparatus for recovering silver and plastic from used film is also disclosed in U.S. Pat. No. 4,392,889 to Grout. In this method, the used film is first passed through a bath preferably comprising a hot caustic solution for precipitating silver layered on the film. The film then passes through a second bath of hot caustic until an adhesive sheet disposed on the film has been dissolved. Typically, the adhesive sheet is made of polyvinylidine chloride which adheres the silver to the film. After a second caustic bath, the film is dried and available for use.

A process for the recovery of clean polyester materials is disclosed in U.S. Pat. No. 3,928,253 to Thornton et al. Specifically, the process is directed to polyester photographic film, where the polyester is coated with binders, adhesives and metal compounds. In order to recover clean polyester, polyester photographic film is first wetted with an aqueous alkaline solution of an organic solvent which loosens and detaches coatings and subcoatings from the surface of the film. The polyester film is then separated from the reagent and rinsed. The reagent is then clarified and recycled and reused on other photographic film.

U.S. Pat. No. 3,652,466 to Hittel et al., discloses another process of recovering the polyester from polyester films. The coated films are cut into small pieces and treated with a caustic aqueous alkali solution to form a slurry. The slurry is fed into a classification column in which the pieces move downward countercurrent to a moving column of aqueous liquid which separates the pieces from the coating material. The pieces are removed from the bottom of the column in suspension and can thereafter be used as a source of polyester material. Further, the coating material can be removed from the top portion of the column and silver halide can be recovered in the form of silver.

Similarly, U.S. Pat. No. 3,647,422 to Wainer discloses the recovery of silver, polyester and amino acids from processed film and U.S. Pat. No. 3,873,314 to Woo et al. discloses the recovery of clean polyester materials from photographic film.

As shown above, the cited prior art methods of recovering waste polyester are generally limited to photographic films. In recycling the photographic films, silver is also recovered, thus making the processes economically viable. Mechanical recovery in non-silver containing polyester films presently lacks such economic advantages.

It has also been discovered that the prior art processes are generally further limited to processing particular types of films. Films containing higher proportionate amounts of non-polyester materials are typically much more difficult and expensive to process. For instance, many post consumer photographic films contain contaminants such as other polymeric materials in amounts up to about 50% by weight. These polymeric materials may include polyvinyl chloride, polyvinylidine chloride, acetate, polystyrene, polyethylene, and other polyolefins. Such films typically cannot be recycled and usually are discarded into landfills.

Recently the focus of recovering polyester from the waste stream has changed from mechanical washing processes to chemically converting the recovered polyester to more useful components. For instance, one current commercial process for chemically recycling polyester is methanolysis. This process is generally directed to the recycling of PET from X-ray and/or photographic film waste. The process involves the steps of: (1) sorting the film from other plastics and papers; (2) grinding the film; (3) washing the film with appropriate chemical solutions; (4) separating the film from a resulting sludge; (5) drying the film in the form of flakes; and (6) reacting the PET flakes with methanol under pressure, in order to convert it to ethylene glycol and dimethyl terephthalate (DMT). However, methanolysis is a very expensive process and can only be used with polyesters that are relatively free of contamination. In fact, many types of PET waste cannot be used due to the high impurity content.

Because of the deficiencies in the prior art, many waste products containing polyesters are not capable of being economically recycled. As such, most polyester waste products end up in landfills. In fact, millions of pounds of polyester-containing products are discarded in landfills each year. Landfill disposal is not only expensive, but is environmentally damaging.

Consequently, the prior art is generally deficient in providing an economical process for the recycling of polyester. The prior art is also deficient in providing a process for the recovery of PET from waste materials containing contaminants and impurities. Further, the prior art is generally deficient in providing a method for recycling PET from products other than photographic and X-ray films. Also, the prior art is generally deficient in providing a method of chemically recycling polyester in which the polyester is converted into more usable chemical components, namely the raw materials from which polyester is formed. Due to the increasing production of waste materials containing polyester, it would be very desirable to have an economically viable process for recycling polyester from the waste stream.

SUMMARY OF THE INVENTION

It is an object of the present invention to provide a process for recycling polyester from waste materials.

It is another object of the present invention to provide a process for chemically recycling polyester by converting it into chemical components.

Still another object of the present invention is to provide a process capable of recovering polyester from materials containing substantial amounts of impurities or contaminants.

It is another object of the present invention to provide a process for recycling polyester without having to first mechanically wash the polyester in order to remove impurities.

Another object of the present invention is to provide a new process for recovering silver from polyester films such as photographic and X-ray films.

These and other objects of the present invention are achieved by providing a process for converting polyester into its original chemical reactants. The process involves the steps of combining materials containing polyester with an alkaline solution to form a slurry. The slurry is indirectly heated to a temperature sufficient to convert the polyester contained within the slurry to disodium terephthalate and ethylene glycol. The heated slurry is then mixed with a quantity of water sufficient to dissolve disodium terephthalate and form an aqueous solution of disodium terephthalic acid.

The process can further include the steps of vaporizing the ethylene glycol upon formation and separating it from the slurry. The evaporated ethylene glycol can then be condensed and collected. Also, the aqueous solution of disodium terephthalic acid can be filtered as desired in order to remove any undissolved solids contained therein. An acid can be added to the resulting filtrate in order to precipitate and recover terephthalic acid from the liquid.

In one embodiment, the alkaline solution combined with the materials containing polyester can be a 50% sodium hydroxide solution and can contain a surfactant or wetting agent. The alkaline solution can be mixed with the materials in a molar ratio of about two moles sodium hydroxide to about one mole terephthalic acid contained within the polyester. The resulting slurry can then be heated to temperatures between about 400° F. to about 600° F. Preferably, this heating step is done in an oxygen-starved environment. Once heated, the slurry can then be mixed with a quantity of water such that the resulting aqueous solution contains from about 40% to about 90% by weight water.

These and other objects are also accomplished by providing a process for recycling waste materials containing polyester. The process includes contacting the waste materials containing a proportionate amount of polyester with a caustic solution of sodium hydroxide to form a slurry. The waste materials may also include contaminants such as organic impurities and metallic impurities. The slurry is heated to temperatures sufficient to saponify the polyester thereby forming a composition comprising disodium terephthalate particulate and ethylene glycol. The composition is then further heated indirectly in order to evaporate the formed ethylene glycol and to carbonize any organic impurities present within the composition. The composition is heated at temperatures insufficient to significantly degrade the disodium terephthalate.

The evaporated ethylene glycol is then separated from the composition. The composition is added to a quantity of water to form an aqueous solution for dissolving the disodium terephthalate therein. The aqueous solution is filtered in order to remove any undissolved contaminants such as any carbonized organic impurities or any metallic impurities. Substantially pure terephalic acid can then be recovered from the aqueous filtrate.

The waste materials entering the process preferably contain at least about 30% by weight polyester. If the materials are contacted with a 50% sodium hydroxide solution, the weight ratio between the alkaline solution and the polyester contained within the waste materials is about 1 to 1. A surfactant can also be added when forming the slurry. The slurry can then be heated to temperatures between about 400° F. to about 600° F. and preferably between about 450° F. to about 550° F.

The process can further include the steps of precipating terephalic acid from the aqueous filtrate by adding an acid thereto. The precipitated terephthalic acid can then be separated, washed and recovered. Also, other materials can be recovered from the undissolved contaminants filtered from the aqueous solution. For instance, if silver is contained within the starting waste materials, the undissolved contaminants can be roasted in order to recover any silver contained therein.

Other objects, features and aspects of the present invention are discussed in greater detail below.

BRIEF DESCRIPTION OF THE DRAWINGS

A full and enabling disclosure of the present invention including the best mode thereof, to one of ordinary skill in the art, is set forth more particularly in the remainder of the specification, including reference to the accompanying figure, in which:

FIG. 1 is a flow chart of one embodiment of the process of the present invention.

DETAILED DESCRIPTION OF PREFERRED EMBODIMENTS

The present invention is generally directed to a process for recycling polyester and in particular PET. Using the process of the present invention, the polyester can be converted into its original chemical reactants such as ethylene glycol and terephthalic acid. The process is primarily directed to using waste materials containing polyester, but is equally applicable to all known polyester-containing materials. Of particular advantage, the materials entering the process of the present invention need not be mechanically washed or chemically treated beforehand. Instead, any contaminants or impurities are separated and removed during the various processing steps. Further, if any valuable substances or metals are included within the contaminants and impurities, those substances can be removed and recovered.

A very general summary of the process of the present invention includes first combining materials containing polyester with an alkaline solution to form a slurry. The slurry is heated, causing the polyester to hydrolize, in part, into disodium terephthalate and ethylene glycol. The ethylene glycol is volitilized and separated from the disodium terephthalate. The separated ethylene glycol is then condensed and collected for further use.

The disodium terephthalate and any other contaminants or impurities that may be present are combined and mixed with water to dissolve the disodium terephthalate. The resulting aqueous solution is then filtered in order to remove any undissolved impurities. In one embodiment, acid can be mixed with the resulting filtrate in order to precipitate terephthalic acid. The terephthalic acid can be separated from the solution, washed, dried and then used as desired in other processes and systems.

The process of the present invention can run continuously or can be set up as a batch system. Again, practically any material containing polyester (or PET) can be processed by the disclosed method. Preferably, the polyester materials are recovered from the solid waste stream, thus alleviating many environmental concerns and disposal problems. Representative materials that can be used in the present invention include but are not limited to developed or undeveloped photographic film and X-ray film, plastic bottles and containers, polymeric adhesive films, saran-bearing polyester films, papers containing polyester, and even polyester and polyester blend fabrics. Currently, such products are being disposed of in landfills after use.

Referring to FIG. 1, one embodiment of the process of the present invention is illustrated on a flowchart. As described above, polyester containing materials 10 can include a wide variety and mixture of articles and can be recovered from the solid waste stream or from other sources. Preferably, the materials contain about thirty percent (30%) by weight polyester or greater, although any materials containing polyester can be processed according to the present method. In particular, blended fabrics containing 40% or 50% polyester may be used in the present process.

Depending on the variety and composition of the materials, materials 10 can be first chopped or ground into a particular size. For instance, photographic film is preferably cut to an average dimension of less than about one inch. Generally, the smaller the size of the material, the less retention time is needed within the process. However, all different sizes and shapes of material may be used within the system of the present invention and no one size or shape is required.

After being sized, materials 10 are combined and mixed with an alkaline solution to form a slurry 20. In one embodiment, materials 10 can be fed to a mixing tank such as a ribbon blender or the like and mixed with the slurry. Preferably, the alkaline solution contains sodium hydroxide, or caustic soda. In one embodiment, the alkaline solution comprises 50% by weight caustic soda and 50% water. Other concentrations may be used in the present invention, however, because caustic strength is generally not a critical factor.

Preferably, materials 10 containing polyester are mixed or contacted with a caustic soda solution in quantities such that the molar ratio of caustic soda to terephthalic acid contained within the polyester is about 2 to 1. When using a 50% caustic solution, the weight ratio between the caustic soda solution and the polyester contained within the materials is normally about 1 to 1. However, depending upon the substances present in materials 10 more or less caustic soda may be added to form slurry 20. Sufficient sodium hydroxide should be present to support a complete reaction with the polyester contained in materials 10 as will be described hereinafter.

Materials 10 and the alkaline solution can be initially combined at ambient temperature and pressure. At this stage in the process, the temperature should not be high enough to degrade or decompose the polyester or to vaporize the alkaline solution.

Optionally, a surfactant or wetting agent may be added to materials 10 and the alkaline solution when forming slurry 20. Addition of a surfactant may facilitate the mixing of the alkaline solution with materials 10 in order to produce a more uniform mixture. The surfactant should be alkaline stable and can be anionic in character. An example of a suitable surfactant is SURMAX CS727 sold by Chemax, Inc. of Greenville, S.C.

After thorough and complete mixing to ensure substantial uniformity, slurry 20 is heated, and preferably heated indirectly as shown at 30. Indirectly heating slurry 20 serves a number of purposes within the process. First, indirectly heating slurry 20 causes the polyester contained therein to hydrolyze or, more specifically, to saponify. As used herein, saponification is the conversion of an ester heated with an alkali into the corresponding alcohol and acid salt. Here, the polyester is converted to disodium terephthalate and ethylene glycol.

The formed disodium terephthalate produced by the reaction is a solid and typically has the appearance of a white tan flake. Ethylene glycol, on the other hand, is a liquid at room temperature.

Besides hydrolyzing and saponifying the polyester, slurry 20 should also be heated to temperatures sufficient to volatilize, or evaporate, the above-formed ethylene glycol. After vaporizing the ethylene glycol, it can be easily separated from the remaining product stream containing the disodium terephthalate. Consequently, slurry 20 should be heated to at least the distillation temperature of ethylene glycol.

At these temperatures, unexpectedly, the disodium terephthalate does not burn, melt or otherwise significantly degrade. As used herein, the term degrade refers to melting, burning, or otherwise changing the physical and chemical characteristics of a substance. However, at these same temperatures, any organic impurities or contaminants present within the product stream can be carbonized. Such impurities would include paper and other wood products, natural fibers such as cotton, polymers such as polyvinyl chloride, polyvinylidene chloride, cellulose acetate, polystyrene, etc. and other combustibles. Upon carbonization, the organic impurities, and particularly the low molecular weight impurities, decompose resulting in a flue gas which also separates from the product stream.

In summary, indirectly heating slurry 20 causes the polyester contained in materials 10 to saponify, resulting in the formation of disodium terephthalate flakes and ethylene glycol. Further, slurry 20 is heated to temperatures sufficient to evaporate the formed ethylene glycol and separate it from the product stream containing the disodium terephthalate. Also, during this heating step, organic impurities present within slurry 20 can be carbonized causing them to decompose.

Preferably, slurry 20 is heated to temperatures capable of volatilizing the ethylene glycol, but at temperatures insufficient to degrade the disodium terephthalate. Specifically, at atmospheric pressure, slurry 20 is optimumly heated to temperatures between from about 400° F. to about 600° F. and preferably between from about 500° F. to about 550° F. Of course, optimum temperatures will depend upon the system conditions and upon the existing pressures. Also, slurry 20 is preferably heated in an oxygen-starved environment. As used herein, oxygen-starved refers to an environment in which oxygen is present below about 19% by volume. Maintaining lower oxygen levels during the heating phase not only protects the disodium terephthalate from being degraded but also prevents against uncontrolled combustion. In particular, oxygen levels should remain lower when cotton, acetate or other flammable substances are present in materials 10.

One method of maintaining lower oxygen levels can include decreasing air flow around the slurry during heating. In another embodiment a blanket of inert gas, such as nitrogen, can be applied to the slurry. Also, the slurry could be heated at reduced pressures corresponding to lower oxygen levels.

Many different and various machinery and processing equipment can be used to heat the slurry. As described above, preferably the slurry is heated indirectly. As such, a heater should be chosen that does not subject its contents to an open flame. Suitable examples of heating devices that can be used in the process of the present invention include ovens, kilns and thermal processors which use hot oil or electrical heating elements to heat their contents. For instance, the Renneburg Division of Heyl and Patterson, Inc. in Pittsburgh, Pa. is currently marketing a multidisc thermal processor. In this device, heat transfer fluids are circulated within hollow disks. A product stream is heated indirectly when contacted with these discs. Of course, many other similar devices are available which may be used in the process of the present invention.

In one embodiment, slurry 20 is indirectly heated in a rotary kiln. The rotary kiln can be heated by an electrical element or by heated oil. The kiln can be heated to temperatures between 400° F. and 600° F. while air flow is controlled therethrough. One example of a suitable indirectly heated kiln for use with the process of the present invention is the Rotary Calciner also marketed by the Renneburg Division of Heyl and Patterson, Inc. Specifically, a Rotary Calciner was successfully tested for use in the process of the present invention. The calciner had a 2 ft. 6 in. diameter, was 32 ft. long, and was heated with an electrical element. Adequate retention times of slurry 20 within the kiln were found to be about 30 to 40 minutes. Of course, if other types of heating equipment were used in the process of the present invention, retention times and other process parameters may be modified.

As described above, while slurry 20 is being heated, evaporated ethylene glycol, the flue gas created by the carbonization of organic contaminants, and water vapor are given off and separated from the product stream. This gaseous composition can then be collected and processed in order to remove and isolate the ethylene glycol as illustrated at 40.

The collected ethylene glycol is a compound used in many processes and applications. Specifically, ethylene glycol is commonly used as an antifreezing agent and, of course, can also be used to manufacture polyester.

As one skilled in the art can appreciate, many different methods for collecting a vapor such as ethylene glycol from a gas stream exist. In one embodiment, the gas stream separated from the product stream of the present invention can be fed to a suitable condenser. Specifically, a partial condenser can be used in which only the ethylene glycol will condense and be collected from the gas stream. The remaining flue gas and water vapor can then be sent to a scrubber or otherwise discharged according to environmental regulations. The liquid ethylene glycol can then be used for other applications as desired.

The product stream separated from the above described gas stream can also be further processed. At this point, the product stream contains disodium terephthalate and possibly contaminants and other impurities. Preferably, the product stream is fed to a mixing tank such as a quench tank and mixed with water in order to dissolve the disodium terephthalate as illustrated at 50.

When mixed with water, disodium terephthalate dissolves along with any salts present in the product stream. However, water insoluble contaminants such as metals, uncarbonized impurities, carbonized organic matter, or unreacted polyester do not dissolve and can be separated from the aqueous solution. This is done by well known separation techniques. The amount of water to be mixed with the product stream varies depending on the various materials present in the product stream and the amount of disodium terephthalate. Specifically, the proportionate amount of water to add can be up to about 90% by weight of the resulting aqueous solution. Under most circumstances, the water should be around 80% by weight of the solution.

After mixing the product stream with water, the next step is to preferably separate out any undissolved impurities as illustrated at 60. Although other methods such as centrifugation would work equally as well, the aqueous solution preferably undergoes filtration which may be more cost effective.

The resulting filter cake filtered from the aqueous solution contains all of the undissolved impurities and contaminants. The filter cake can be discarded or can be incinerated. However, if any useful materials are present within the filter cake, they can be separated and recovered. For instance, developed and undeveloped photographic films contain silver which is considered a precious metal. If silver-bearing materials enter into the process of the present invention, the silver will be collected in this filter cake. In one embodiment, the filter cake can be roasted in a kiln at high temperatures such as around 1500° C. to incinerate most of the composition and leave behind silver powder. As such, the present invention is also directed to a new and useful process for the recovery of silver from polyester film materials. Of course, the silver can also be separated by other means as can be appreciated by one skilled in the art.

After separating out the undissolved impurities, the resulting aqueous filtrate comprises water, dissolved disodium terephthalate and the dissolved salts. Depending upon the content of the starting materials used in the process, the filtrate can be used in other processes without further treatment. However, preferably terephthalic acid is precipitated and recovered from the solution as is shown at 70. Again, many different methods and processes exist for separating terephthalic acid from an aqueous solution. In one embodiment, the filtrate can be acidified causing terephthalic acid of high purity to be precipitated. In order to acidify the filtrate, hydrochloric acid can be added. Once the terephthalic acid precipitates, the terephthalic acid can be filtered, washed and dried, leaving a relatively pure product. The product can be further purified using methods known by those skilled in the art if necessary.

The remaining filtrate solution contains water and, possibly, some salts such as sodium chloride. This solution can be further treated and disposed. Also, the sodium chloride can be recovered and reused if desired.

It is to be understood that the above description is a description of a preferred embodiment of the process of the present invention and does not embrace all variables that may be practiced. For instance, other optional steps can be added to the process in order to enhance performance and to achieve a desired result. For instance, while the process is preferably carried out in a continuous manner, a batch system may be just as effective. In one embodiment, a pan may be used to heat slurry 20 to the required temperatures inside of an oven. However, in a batch system, retention times may increase and the quantity of material being processed at a particular time may have to be decreased.

Another option for the process of the present invention is to include a recycle or return stream as shown in phantom in FIG. 1 in order to further purify resulting products. For instance, the undissolved impurities and contaminants separated from the aqueous filtrate could be mixed with more caustic to form a slurry and then processed as before. By running these solids through the process multiple times, the concentration of impurities, such as silver, will increase in the filter cake. Further, a higher percentage of the polyester contained in materials 10 may be processed.

In another embodiment, an activated carbon filter can be used to filter the aqueous solution of disodium terephthalate. Use of a carbon filter is well known and will further purify the aqueous filtrate.

The present invention may be better understood by reference to the following examples.

EXAMPLE I

Four Hundred and Sixty-five (465) pounds of developed lithographic film were ground to an average dimension of 3 to 10 millimeters and continuously fed into a process in accordance with the present invention. The ground lithographic film was first added to a ribbon blender and mixed with 488 pounds of 50% caustic soda and water and 0.2 pounds of an alkali stable anionic surfactant. The ribbon blender used was the Horizontal Blender #250 sold by Young Industries of Muncy, Pa. The surfactant was SURMAX CS727 sold by Chemax, Inc. of Greenville, S.C. The film, the caustic soda and the surfactant were mixed until the film was evenly coated.

From the ribbon blender, the mixture was then fed into an externally heated rotary kiln via a screw conveyor. The rotary kiln used was the above described Rotary Calciner sold by Heyl & Patterson, Inc., Renneburg Division of Pittsburgh, Pa. The shell temperature of the rotary kiln was maintained at 550° F. The polyester contained in the film was converted into ethylene glycol and disodium terephthalate. The ethylene glycol that was formed was evaporated and was removed from the kiln by flowing air therethrough. Ultimately, the ethylene glycol was condensed and collected using a partial condenser. Water vapor produced within the kiln was allowed to pass through the condensor and into a scrubber system. One Hundred and Sixty (160) pounds of ethylene glycol were collected. The retention time of the mixture in the heated zone of the kiln was approximately 30 minutes.

The resultant solid material from the kiln was in the form of a tan granular powder. The yield of solid material from the kiln was 475 pounds. This material was added to 1900 pounds of water in order to dissolve the disodium terephthalate. The aqueous solution was then passed through a filter in order to remove any undissolved impurities.

The filter cake, after being dried, weighed 56 pounds and contained 9% by weight silver. The filter cake was then roasted at 1250° F. and smelted in order to recover pure silver.

Five Hundred and nineteen (519) pounds of 32% hydrochloric acid was then added to the filtrate in order to adjust the pH to 3.5. A precipitate formed as the acid was added. This precipitate was removed using a filter and washed with 1000 pounds of fresh water. After drying, the precipitate was analyzed and found to be at least 98% terephthalic acid. The yield of terephthalic acid was 370 pounds.

EXAMPLE II

The process of the present invention was also tested in a batch system. Specifically, 84 pounds of nonsilver-bearing PET film coated with an adhesive polymer formed from copolymers of polyvinylidene chloride and polyvinyl chloride were ground to an average dimension of about 1 to 2 millimeters. The ground PET film was charged to a mixer and 42 pounds of dry caustic soda and 32 pounds of water were added. Mixing was continued until the film was evenly coated. This mixture was then added to a steel pan and placed in an oven at 450° F. for two hours. Ethylene glycol vapor and other gases given off during heating were removed from the oven by an air sweep and passed to a scrubber system.

The remaining solid product in the pan after heating weighed 94 pounds. This product was added to 375 pounds of water and filtered. After drying, the filter cake weighed 2.5 pounds. Seventy-eight (78) pounds of 32% hydrochloric acid was then added to the filtrate to adjust the pH to 3.5. A white/tan precipitate formed as the acid was added. The precipitate was removed by filtration and washed with 200 pounds of fresh water. After being dried, the precipitate was analyzed and found to be at least 98% terephthalic acid. The yield of terephthalic acid was 68 pounds.

EXAMPLE III

The following test was performed in order to ensure that polyester cloth materials can also be processed in accordance with the present invention. Specifically, 26.8 parts of blue wipes were cut into approximately ½" squares. A blue wipe is a fabric made from a blend of polyester and paper. The cut blue wipe squares were combined and mixed with 26.8 parts of a 50% sodium hydroxide solution, 0.2 parts of the SURMAX CS727 surfactant used in Example I and 10 parts of water. The resulting slurry was placed in an oven at 300° C. for 30 minutes. After 30 minutes, the paper was charred and appeared to have burned.

After heating, the resultant material was mixed with water and filtered. The filtrate was acidified, causing a white precipitate to form. The precipitate was analyzed and found to be terephthalic acid.

It will be understood that the invention is not limited to any specific parameters, amounts or process steps described herein, and that any method employing agents equivalent to those described falls within the scope of the present invention. It will be understood that while the form of the invention shown and described herein constitutes a preferred embodiment of the invention, it is not intended to illustrate all possible forms of the invention. In addition, it should be understood that aspects of the various embodiments may be interchanged both in whole or in part. The words used are words of description rather than of limitation. Various changes and variations may be made to the present invention without departing from the spirit and scope of the following claims.

What is claimed is:

1. A process for converting polyester into its original chemical reactants, said process comprising the steps of:
    combining materials containing polyethylene terephthalate with an alkaline solution to form a slurry;
    heating said slurry to a temperature sufficient to convert said polyethylene terephthalate contained within said slurry to disodium terephthalate and ethylene glycol, wherein said temperature is at the distillation temperature of ethylene glycol; and
    mixing said heated slurry with a quantity of water sufficient to dissolve said disodium terephthalate and form an aqueous solution of disodium terephthalic acid.

2. The process as defined in claim 1, wherein said alkaline solution is a 50% sodium hydroxide solution and wherein said alkaline solution is combined with said materials in a molar ratio of about 2 moles sodium hydroxide to about 1 mole terephthalic acid contained in said polyester.

3. The process as defined in claim 1, wherein a surfactant is also combined with said materials and said alkaline solution when forming said slurry.

4. The process as defined in claim 1, wherein said slurry is indirectly heated to a temperature of from about 400° F. to about 600° F.

5. The process as defined in claim 1, wherein said slurry is indirectly heated in an oxygen starved environment.

6. The process as defined in claim 1, further comprising the step of separating said vaporized ethylene glycol from said slurry.

7. The process as defined in claim 6, wherein said separated ethylene glycol is condensed and collected.

8. The process as defined in claim 1, wherein said aqueous solution formed by mixing said heated slurry with said quantity of water contains from about 40% to about 90% by weight water.

9. The process as defined in claim 1, further comprising the step of separating any undissolved solids from said aqueous solution resulting in a liquid product containing dissolved disodium terephthalic acid.

10. The process as defined in claim 9, wherein said undissolved solids are separated from said aqueous solution by filtration.

11. The process as defined in claim 9, wherein said undissolved solids are separated from said aqueous solution by centrifugation.

12. The process as defined in claim 1, further comprising the step of precipitating terephthalic acid from said aqueous solution by adding an acid thereto and further separating said precipitated terephthalic acid from said solution.

13. A process for recycling waste materials containing polyethelene terephthalate, said process comprising the steps of:
    contacting the waste materials with a caustic solution of sodium hydroxide to form a slurry, said waste materials containing a proportionate amount of polyethylene terephthalate, organic, and metallic impurities;
    heating said slurry to temperatures sufficient to saponify said polyester thereby forming a composition comprising disodium terephthalate particulate and ethylene glycol wherein said temperature is at the distillation temperature of ethylene glycol;
    indirectly heating said composition further to evaporate said formed ethylene glycol and to carbonize any organic impurities present within said composition without degrading said disodium terephthalate;
    separating said evaporated ethylene glycol from said composition;
    adding said composition to a quantity of water to form an aqueous solution for dissolving said disodium terephthalate therein; and
    filtering said aqueous solution in order to remove any undissolved contaminants, including any said carbonized organic impurities and any said metallic impurities, resulting in an aqueous filtrate from which substantially pure terephthalic acid can be recovered.

14. The process as defined in claim 13, wherein said waste materials contain at least 30% by weight polyester.

15. The process as defined in claim 13, wherein said slurry is heated in an oxygen-starved environment.

16. The process as defined in claim 13, wherein said caustic solution comprises a sodium hydroxide solution of about 50%, and wherein said caustic solution is contacted with said waste materials in a weight ratio of about 1 to 1.

17. The process as defined in claim 13, wherein a surfactant is mixed with said waste materials and said caustic solution, said surfactant being anionic and alkaline stable.

18. The process as defined in claim 13, wherein said separated ethylene glycol is condensed and collected.

19. The process as defined in claim 13, wherein said slurry is heated to temperatures between about 450° F. to about 550° F.

20. The process as defined in claim 13, wherein silver is present in said waste materials and is separated and recovered from said filtered contaminants.

21. The process as defined in claim 13, further comprising the steps of precipitating terephthalic acid from said aqueous filtrate by adding an acid thereto and further separating said precipitated terephthalic acid from said filtrate.

22. A process for chemically recycling waste materials that contain polyethylene terephthalate, said process comprising the steps of:
    providing waste materials;

combining said materials with a solution of sodium hydroxide to form an alkaline mixture;

heating said mixture to temperatures between about 400° F. to about 600° F., wherein certain of said polyester contained within said mixture is chemically converted to ethylene glycol vapor and disodium terephthalate particulate;

separating and collecting said ethylene glycol vapor from said mixture;

dissolving said disodium terephthalate in an aqueous solution by combining said mixture with a fluid containing water; and filtering said aqueous solution in order to remove any undissolved matter contained therein, wherein terephthalic acid is recovered from said filtered solution.

23. The process as defined in claim 22, wherein said solution of sodium hydroxide is a 50% by volume sodium hydroxide solution which is combined with said materials in a weight ratio of about 1 to 1.

24. The process as defined in claim 22, wherein a surfactant is also combined with said materials and with said solution of sodium hydroxide.

25. The process as defined in claim 22, wherein said undissolved matter filtered from said aqueous solution is roasted in order to recover any silver contained therein.

26. The process as defined in claim 22, wherein said mixture is heated indirectly in an oxygen-starved environment.

27. The process as defined in claim 22, further comprising the steps of precipitating terephthalic acid from said filtered aqueous solution by adding hydrochloric acid thereto and filtering said aqueous solution in order to separate said precipitated terephthalic acid.

* * * * *